United States Patent
Hefetz et al.

(10) Patent No.: US 10,143,437 B2
(45) Date of Patent: Dec. 4, 2018

(54) SYSTEMS AND METHODS FOR DYNAMIC SCANNING WITH MULTI-HEAD CAMERA

(71) Applicant: General Electric Company, Schenectady, NY (US)

(72) Inventors: Yaron Hefetz, Tirat Carmel (IL); Jean-Paul Bouhnik, Tirat Carmel (IL)

(73) Assignee: General Electric Company, Schenectady, NY (US)

( * ) Notice: Subject to any disclaimer, the term of this patent is extended or adjusted under 35 U.S.C. 154(b) by 448 days.

(21) Appl. No.: 14/788,180

(22) Filed: Jun. 30, 2015

(65) Prior Publication Data

US 2017/0000448 A1    Jan. 5, 2017

(51) Int. Cl.
*A61B 6/00* (2006.01)
*A61B 6/03* (2006.01)

(52) U.S. Cl.
CPC .............. *A61B 6/545* (2013.01); *A61B 6/037* (2013.01); *A61B 6/4266* (2013.01); *A61B 6/4429* (2013.01); *A61B 6/52* (2013.01)

(58) Field of Classification Search
CPC ....... A61B 6/545; A61B 6/037; A61B 6/4266; A61B 6/4429; A61B 6/52
See application file for complete search history.

(56) References Cited

U.S. PATENT DOCUMENTS

| | | | |
|---|---|---|---|
| 5,376,796 A | * | 12/1994 | Chan ................. G01B 11/2433 250/363.02 |
| 6,140,650 A | | 10/2000 | Berlad |
| 6,239,438 B1 | | 5/2001 | Schubert |
| 6,388,244 B1 | | 5/2002 | Gagnon |
| 6,535,229 B1 | | 3/2003 | Kraft |
| 6,748,044 B2 | | 6/2004 | Sabol et al. |

(Continued)

FOREIGN PATENT DOCUMENTS

| | | |
|---|---|---|
| WO | 2008135994 A2 | 11/2008 |
| WO | 2009036078 A2 | 3/2009 |

OTHER PUBLICATIONS

A PCT Search Report and Written Opinion issued in connection with corresponding Application No. PCT/IL2014/050848 dated Feb. 5, 2015.

(Continued)

*Primary Examiner* — Tse Chen
*Assistant Examiner* — Joanne Hoffman
(74) *Attorney, Agent, or Firm* — Dean D. Small; The Small Patent Law Group, LLC

(57) ABSTRACT

A nuclear medicine (NM) multi-head imaging system is provided that includes a gantry, plural detector units, and at least one processor. The gantry defines a bore configured to accept an object to be imaged. The plural detector units are mounted to the gantry. Each detector unit defines a corresponding view oriented toward a center of the bore, and is configured to acquire imaging information over a sweep range. The at least one processor is configured to dynamically determine at least one boundary of an acquisition range corresponding to an uptake value of the object to be imaged for at least one of the detector units. The acquisition range is smaller than sweep range. The at least one processor is also configured to control the at least one detector unit to acquire imaging information over the acquisition range.

20 Claims, 7 Drawing Sheets

(56) References Cited

U.S. PATENT DOCUMENTS

| | | | |
|---|---|---|---|
| 6,943,355 B2 | 9/2005 | Schwartz et al. | |
| 7,026,623 B2 | 4/2006 | Oaknin et al. | |
| 7,381,959 B2 | 6/2008 | Manjeshwar et al. | |
| 7,668,288 B2 * | 2/2010 | Conwell | A61B 6/032 378/16 |
| 7,671,331 B2 | 3/2010 | Hefetz | |
| 8,280,124 B2 | 10/2012 | Dichterman et al. | |
| 8,492,725 B2 * | 7/2013 | Zilberstein | G01T 1/1611 250/363.04 |
| 2002/0191828 A1 | 12/2002 | Colbeth et al. | |
| 2003/0054563 A1 * | 3/2003 | Ljungstrom | G01N 21/6402 436/172 |
| 2003/0153830 A1 * | 8/2003 | Weinberg | A61B 6/0414 600/436 |
| 2004/0021082 A1 * | 2/2004 | Wong | G01T 1/1644 250/367 |
| 2004/0174949 A1 * | 9/2004 | Yamashita | A61N 5/10 378/65 |
| 2005/0145797 A1 | 7/2005 | Oaknin et al. | |
| 2005/0251010 A1 * | 11/2005 | Mistretta | A61B 6/025 600/407 |
| 2006/0108532 A1 | 5/2006 | Ohana et al. | |
| 2006/0113482 A1 * | 6/2006 | Pelizzari | A61N 5/1049 250/370.09 |
| 2006/0249682 A1 * | 11/2006 | Hogg | G01T 1/2985 250/363.03 |
| 2007/0018108 A1 | 1/2007 | Kitamura | |
| 2007/0025522 A1 * | 2/2007 | Fenster | A61B 6/032 378/167 |
| 2007/0173719 A1 * | 7/2007 | Haider | G16H 50/50 600/431 |
| 2008/0001090 A1 * | 1/2008 | Ben-Haim | G01T 1/1648 250/363.08 |
| 2008/0029704 A1 * | 2/2008 | Hefetz | A61B 6/037 250/363.01 |
| 2008/0033291 A1 * | 2/2008 | Rousso | A61B 5/02755 600/436 |
| 2008/0039721 A1 * | 2/2008 | Shai | A61B 6/032 600/436 |
| 2008/0092074 A1 | 4/2008 | Cohen | |
| 2009/0070121 A1 | 3/2009 | Leonelli et al. | |
| 2010/0261997 A1 * | 10/2010 | Ren | A61B 6/037 600/424 |
| 2010/0308817 A1 * | 12/2010 | Vija | A61B 6/037 324/307 |
| 2011/0026685 A1 * | 2/2011 | Zilberstein | G01T 1/1611 378/197 |
| 2011/0103544 A1 * | 5/2011 | Hermony | A61B 6/032 378/19 |
| 2011/0147594 A1 * | 6/2011 | Scoullar | A61B 6/037 250/362 |
| 2011/0240865 A1 * | 10/2011 | Frach | G01T 1/2018 250/362 |
| 2012/0108948 A1 * | 5/2012 | Jansen | A61B 6/037 600/411 |
| 2012/0205542 A1 | 8/2012 | Goedicke et al. | |
| 2013/0168567 A1 | 7/2013 | Wartski et al. | |
| 2014/0126793 A1 | 5/2014 | Ahn et al. | |
| 2014/0158890 A1 * | 6/2014 | Pistorius | G01T 1/1647 250/362 |
| 2014/0163368 A1 * | 6/2014 | Rousso | A61B 6/037 600/436 |
| 2014/0343400 A1 * | 11/2014 | Takayama | A61B 6/4258 600/411 |
| 2017/0014096 A1 | 1/2017 | Bouhnik et al. | |

OTHER PUBLICATIONS

Meikle et al., "Accelerated EM reconstruction in total-body PET: potential for improving tumour detectability," 1994, Physics in Medicine and Biology, vol. 39, pp. 1689-1704.

Park et al, "Performance of a high-sensitivity dedicated cardiac SPECT scanner for striatal uptake quantification in the brain based on analysis of projection data," Med. Phys. 40 (4), Apr. 2013.

Riddell et al., "Noise reduction in oncology FDG PET images by iterative reconstruction: a quantitative assessment," 2001, the Journal of Nuclear Medicine, vol. 42, No. 9, pp. 1316-1323.

Shepp et al., "Maximum likelihood reconstruction for emission tomography," 1982, IEEE Transaction on Medical Imaging, vol. MI-1, No. 2, pp. 113-121.

* cited by examiner

SYSTEMS AND METHODS FOR DYNAMIC SCANNING WITH MULTI-HEAD CAMERA

BACKGROUND

The subject matter disclosed herein relates generally to medical imaging systems, and more particularly to calibration of radiation detection systems.

In nuclear medicine (NM) imaging, such as single photon emission computed tomography (SPECT) or positron emission tomography (PET) imaging, radiopharmaceuticals are administered internally to a patient. Detectors (e.g., gamma cameras), typically installed on a gantry, capture the radiation emitted by the radiopharmaceuticals and this information is used, by a computer, to form images. The NM images primarily show physiological function of, for example, the patient or a portion of the patient being imaged.

An NM imaging system may be configured as a multi-head imaging system having a number of individual detectors distributed about the gantry. Each detector may pivot or sweep to provide a range over which the detector may acquire information that is larger than a stationary field of view of the detector. However, as a detector sweeps through a range, the detector may acquire imaging information that is not of interest, or not as useful as information from a region of interest that is covered by only a portion of a range. The time spent by the detector collecting information that is not of interest may result in an inefficient acquisition time.

BRIEF DESCRIPTION

In accordance with an embodiment, a nuclear medicine (NM) multi-head imaging system is provided that includes a gantry, plural detector units, and at least one processor. The gantry defines a bore configured to accept an object to be imaged. The plural detector units are mounted to the gantry. Each detector unit defines a corresponding view oriented toward a center of the bore, and is configured to acquire imaging information over a sweep range corresponding to the corresponding view. The at least one processor is operably coupled to at least one of the detector units, and configured to dynamically determine, during a primary image acquisition configured to obtain information for reconstructing an image, at least one boundary of an acquisition range corresponding to an uptake value of the object to be imaged for at least one of the detector units, wherein the acquisition range is smaller than sweep range. The at least one processor is also configured to control the at least one detector unit to acquire imaging information over the acquisition range.

In accordance with another embodiment, a method includes acquiring imaging information with plural detector units mounted to a gantry defining a bore configured to accept an object to be imaged, each detector unit defining a corresponding view oriented toward a center of the bore and configured to acquire the imaging information over a sweep range corresponding to the corresponding view. The method also includes dynamically determining, during a primary image acquisition configured to obtain information for reconstructing an image, at least one boundary of an acquisition range corresponding to an uptake value of the object to be imaged for at least one of the detector units, wherein the acquisition range is smaller than sweep range. Further, the method includes controlling the at least one detector unit to acquire imaging information over the acquisition range.

In accordance with another embodiment, a tangible and non-transitory computer readable medium comprising one or more software modules configured is provided. The one or more software modules are configured to direct one or more processors to: acquire imaging information with plural detector units mounted to a gantry defining a bore configured to accept an object to be imaged, each detector unit defining a corresponding view oriented toward a center of the bore and configured to acquire the imaging information over a sweep range corresponding to the corresponding view: dynamically determine, during a primary image acquisition configured to obtain information for reconstructing an image, at least one boundary of an acquisition range corresponding to an uptake value of the object to be imaged for at least one of the detector units, wherein the acquisition range is smaller than sweep range; and control the at least one detector unit to acquire imaging information over the acquisition range.

DETAILED DESCRIPTION

Figure 1:
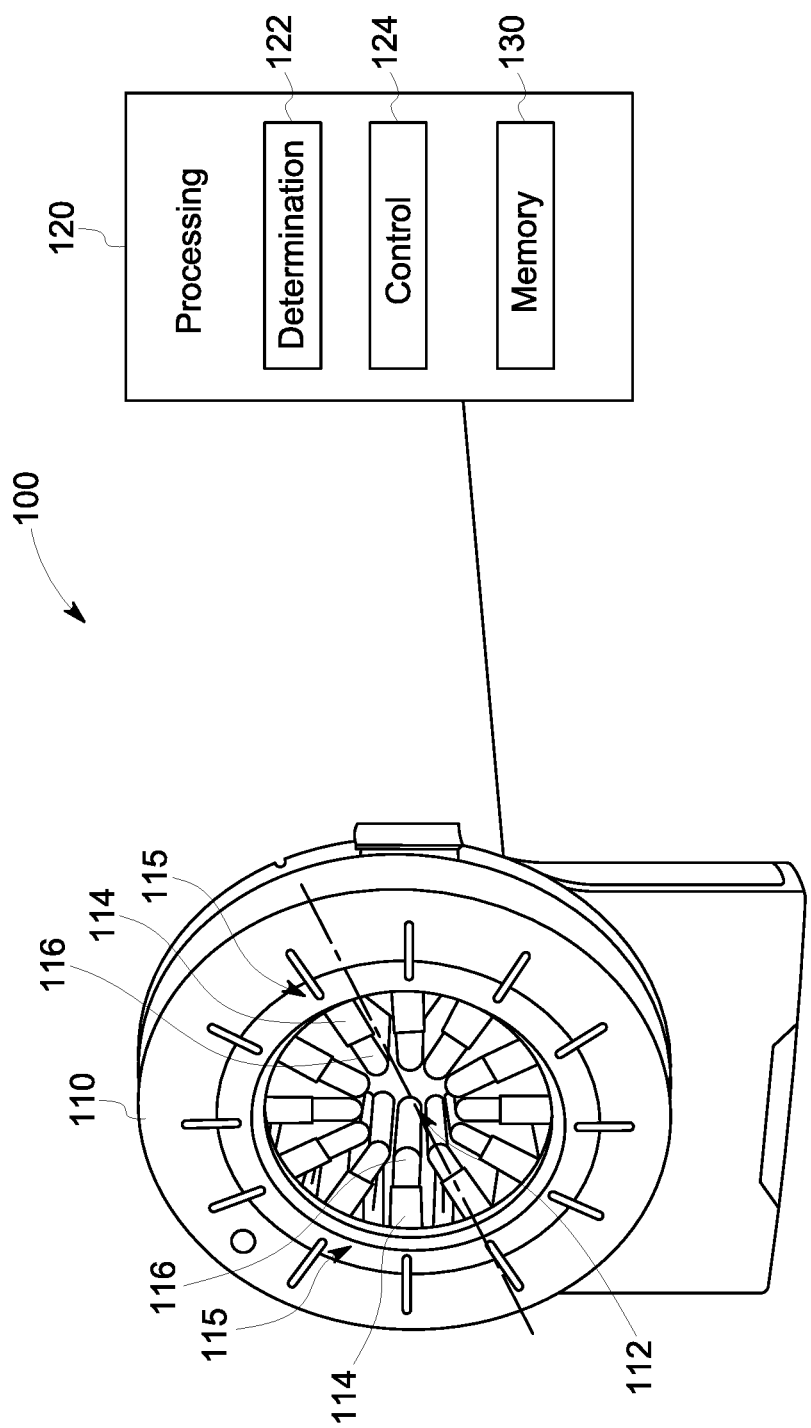
FIG. 1 provides a schematic view of a nuclear medicine (NM) imaging system according to an embodiment.

The foregoing summary, as well as the following detailed description of certain embodiments and claims, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. Various modules or units shown in the attached figures may represent the hardware that operates based on software or hardwired instructions, the software that directs hardware to perform the operations, or a combination thereof.

"Systems," "units," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

As used herein, an element or step recited in the singular and preceded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Various embodiments provide systems and methods for reducing acquisition time and/or improving image quality for NM imaging systems including at least one detector that sweeps over a range during image acquisition.

For example, in some embodiments, detectors of a multi-head camera begin scanning a patient with the heads of the detectors at an extreme view angle (e.g., at an edge or boundary of a sweep range). It may be noted that in other embodiments the detector heads may begin at other positions, which may be different for each detector head. During the first cycle or sweep of the detectors over a range, a processor receiving information (e.g., photon counts) from the detectors monitors the received information. When the activity (e.g., photon counts) corresponding to a region of interest of the patient comes into view of a sweeping detector, the processor dynamically marks the view angle as a start of an acquisition range. The heads continue to pivot and the processor continues to monitor collected information. When the activity comes out of view, the processor dynamically marks the corresponding view angle as the end of the acquisition range. The pivot direction may then be reversed and the head scans from the end of the acquisition range to the start of the range. In some embodiments, the pivot direction may be reversed again and the head scans from the start of the range to the end of the range. The process may repeat a number of times until a desired amount of imaging information has been collected.

In some embodiments, a user may input at least one numerical patient parameter, such as one or more of weight, head radius, head circumference, body mass index, or the like. Additionally or alternatively, at least one numerical patient parameter may be accessed from a patient file. A processor of the imaging system may then calculate a patient adapted initial starting point for the scan based on the one or more numerical patient parameters.

A technical effect of at least one embodiment includes improved image quality. A technical effect of at least one embodiment includes reduced acquisition time.

FIG. 1 provides a schematic view of a nuclear medicine (NM) multi-head imaging system 100 in accordance with various embodiments. Generally, the imaging system 100 is configured to acquire imaging information (e.g., photon counts) from an object to be imaged (e.g., a human patient) that has been administered a radiopharmaceutical. The depicted imaging system 100 includes a gantry 110 and a processing unit 120.

The gantry 100 defines a bore 112. The bore 112 is configured to accept an object to be imaged (e.g., a human patient or portion thereof). As seen in FIG. 1, plural detector units 115 are mounted to the gantry 110. In the illustrated embodiment, each detector unit 115 includes an arm 114 and a head 116. The arm 114 is configured to articulate the head 116 radially toward and/or away from a center of the bore 112 (and/or in other directions), and the head 116 includes at least one detector, with the head 116 disposed at a radially inward end of the arm 114 and configured to pivot to provide a range of positions from which imaging information is acquired.

The detector of the head 116, for example, may be a semiconductor detector. For example, a semiconductor detector various embodiments may be constructed using different materials, such as semiconductor materials, including Cadmium Zinc Telluride (CdZnTe), often referred to as CZT, Cadmium Telluride (CdTe), and Silicon (Si), among others. The detector may be configured for use with, for example, nuclear medicine (NM) imaging systems, positron emission tomography (PET) imaging systems, and/or single photon emission computed tomography (SPECT) imaging systems.

In various embodiments, the detector may include an array of pixelated anodes, and may generate different signals depending on the location of where a photon is absorbed in the volume of the detector under a surface if the detector. The volumes of the detector under the pixelated anodes are defined as voxels (not shown). For each pixelated anode, the detector has a corresponding voxel. The absorption of photons by certain voxels corresponding to particular pixelated anodes results in charges generated that may be counted. The counts may be correlated to particular locations and used to reconstruct an image.

Figure 2:
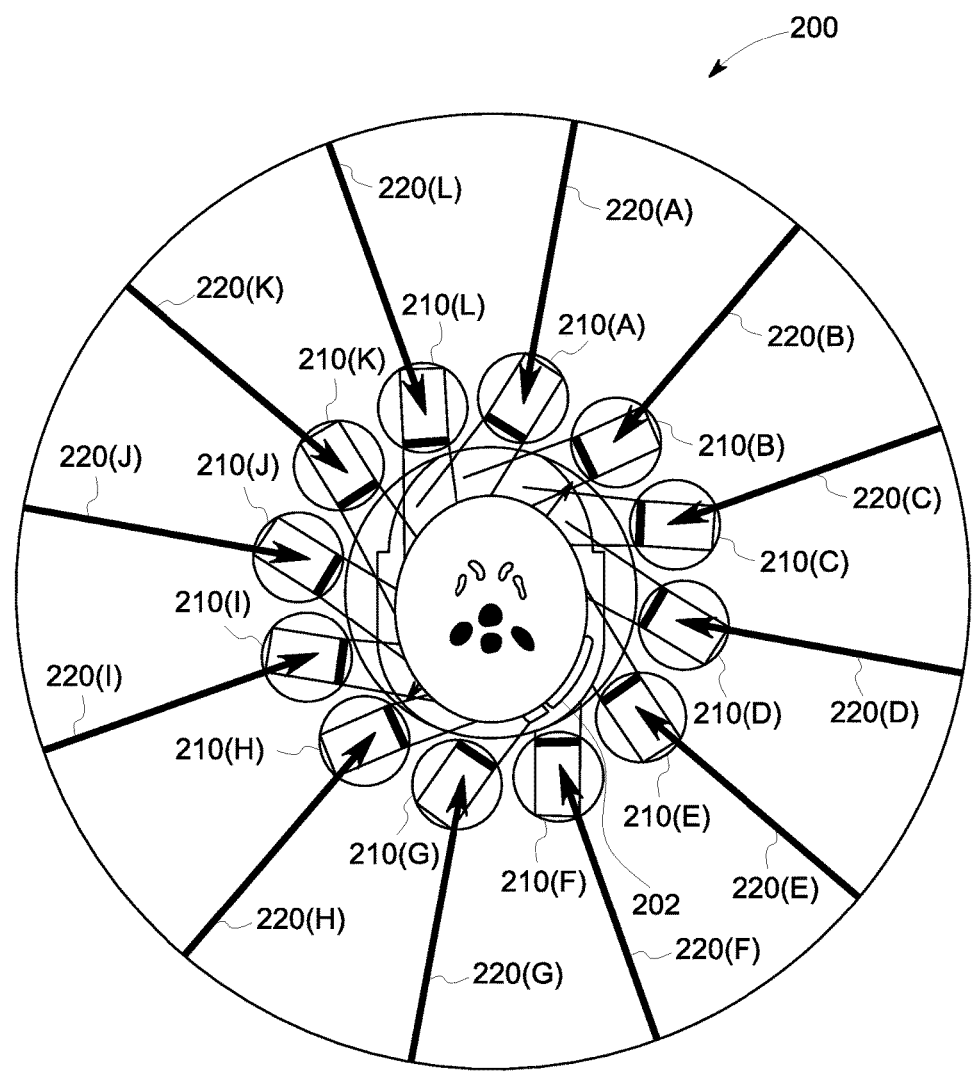
FIG. 2 provides a schematic view of a detector arrangement according to an embodiment.

In various embodiments, each detector unit 115 may define a corresponding view that is oriented toward the center of the bore 112. Each detector unit 115 in the illustrated embodiment is configured to acquire imaging information over a sweep range corresponding to the view of the given detector unit. FIG. 2 illustrates a detector arrangement 200 in accordance with various embodiments. The detector units of FIG. 1, for example, may be arranged in accordance with aspects of the detector arrangement 200.

As seen in FIG. 2, the detector arrangement 200 includes detector units 210(a), 210(b), 210(c), 210(d), 210(e), 210(f), 210(g), 210(h), 210(i), 210(j), 210(k), 210(l) disposed about and oriented toward (e.g., a detection or acquisition surface of the detector units, and/or the collimator's FOV (Field Of View), are oriented toward) an object 202 to be imaged in the center of a bore. Each detector unit of the illustrated embodiment defines a corresponding view that is oriented toward the center of the bore of the detector arrangement 200. The view for each detector unit 210, for example, may be aligned along a central axis of a corresponding arm (e.g., arm 114) of the detector unit 210. In the illustrated embodiment, the detector unit 210(a) defines a corresponding view 220(a), the detector unit 210(b) defines a corresponding view 220(b), the detector unit 210(c) defines a corresponding view 220(c), and so on. The detector units 220 are configured to sweep or pivot (thus sweeping the corresponding FOV's) over a sweep range (or portion thereof) bounded on either side of a line defined by the corresponding view during acquisition of imaging information. Thus, each detector unit 210 may collect information over a range larger than a field of view defined by a stationary detector unit. It may be noted that, generally, the sweeping range that a detector may pivot may be larger than the corresponding view during acquisition. In some cameras, the sweeping range that a detector may pivot may be unlimited (e.g., the detector may pivot a full 360 degrees).

With continued reference to FIG. 1, the depicted processing unit 120 is configured to dynamically determine, during a primary image acquisition, at least one boundary of an acquisition range corresponding to an uptake value of an object to be imaged for at least one of the detector units 115. The acquisition range is smaller than the sweep range, or maximum range of coverage, of the at least one detector unit 115. A primary image acquisition, as used herein, may be understood as a scanning procedure or process used to collect imaging information for reconstruction of an image. The primary image acquisition may, for example, be performed over a specified time period or to collect a specified number of counts corresponding to an amount of information sufficient to provide a diagnostically useful resolution. For the purposes of clarity and avoidance of doubt, a scout scan, or other "pre-scan" utilized for the purposes of locating an organ or portion thereof and/or for positioning imaging equipment but not used in reconstruction of an image used for diagnostic purposes, are not examples of a primary image acquisition. The processing unit 120 is also configured to control the at least one detector unit 115 to acquire imaging information over the acquisition range.

Figure 3:
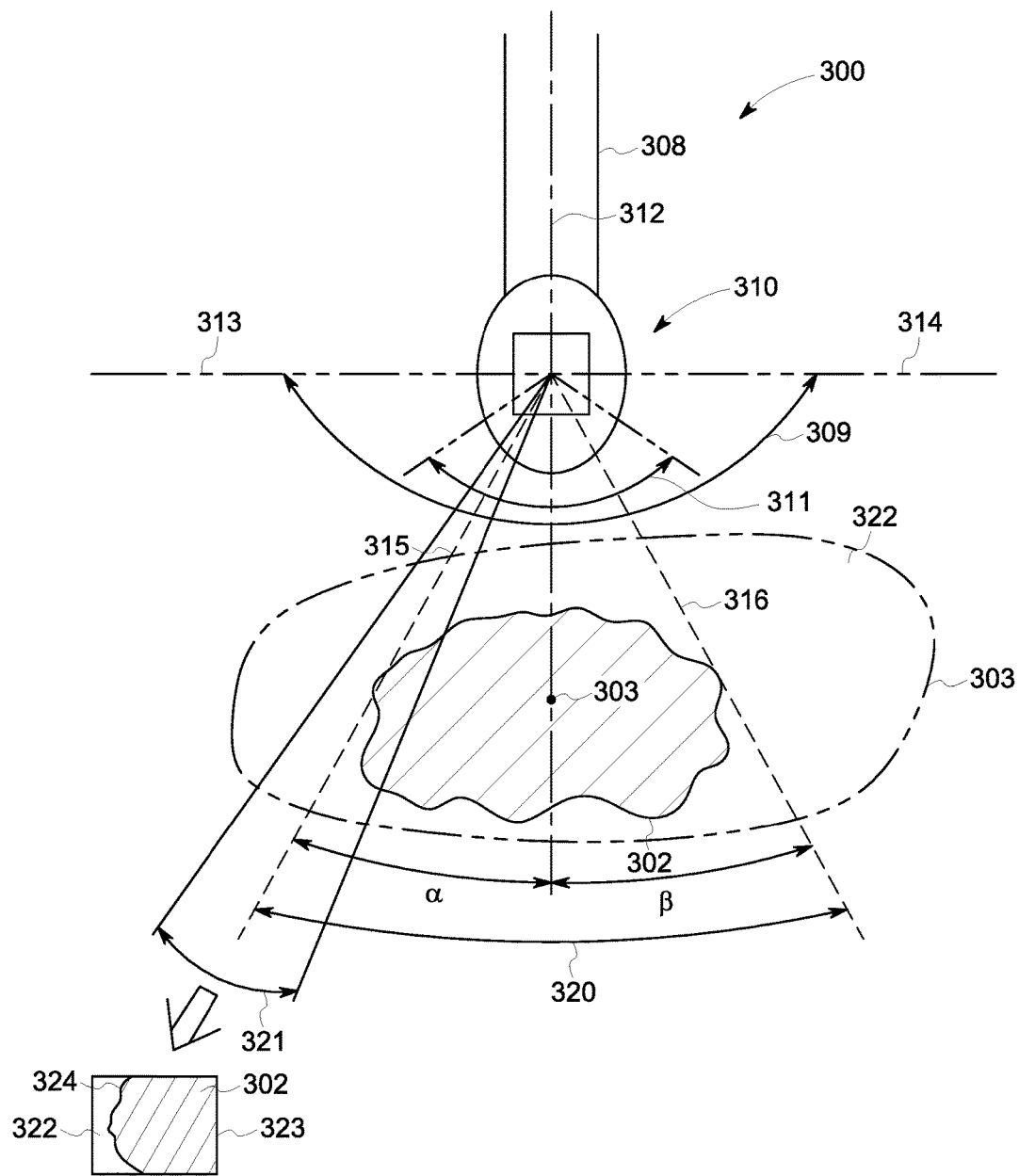
FIG. 3 depicts sweep and acquisition ranges for a detector unit according to an embodiment.

FIG. 3 depicts sweep and acquisition ranges for a detector unit 300 according to various embodiments. As seen in FIG. 3, the detector unit 300 includes a detector head 310 disposed at an end of a detector arm 308. In FIG. 3, only one detector unit 300 is depicted for ease and clarity of illustration. It may be noted that the detector unit 300 may be part of an arrangement of plural detector heads, such as depicted in FIGS. 1 and 2, and that the general principles discussed in connection with the detector unit 300 may be applied to one or more additional detector units of a multi-head camera imaging system. In FIG. 3, the detector unit 300 may be used to acquire imaging information (e.g., photon counts) of an object 303 having a region of interest 302. In the illustrated embodiment, the region of interest 302 (or ROI 302) is surrounded by surrounding tissue 322. The region of interest 302, for example, may be an organ such as the heart or brain (or portion thereof), and may have a substantially larger uptake of an administered radiopharmaceutical than surrounding tissue 322 of the object 303. A central axis 312 of the detector unit 300 passes through a center 304 of the region of interest 302 (which is disposed at the center of a bore in the illustrated embodiment). The central axis 312, for example, may correspond to a line along the view corresponding to the detector unit 300 when the detector unit 300 is at a midpoint of a range of coverage of the detector unit 300, and/or may be aligned with a central axis of the detector arm 308 to which the detector head 310 is attached.

In the illustrated embodiment, the detector unit 300 is depicted as aligned with the central axis 312, and may be rotated, pivoted or swept over a sweep range 309 between a first limit 313 and a second limit 314. In the illustrated embodiment, the first limit 313 and the second limit 314 define a sweep range 309 (or maximum range of coverage) of 180 degrees. In other embodiments, the sweep range 309 and/or relative positions of the first limit 313 and second limit 314 may vary from the depicted arrangement. It may be noted that the sweep range 309 provides more coverage than is required to collect imaging information of the region of interest 302. Thus, if the detector unit 300 is swept over the sweep range 309 during a duration of an imaging acquisition, information that may be not be useful for diagnostic purposes (e.g., information towards the ends of the sweep range 309 that does not include information from the region of interest 302) may be collected. The time used to collect the information that is not useful for diagnostic purposes may be more efficiently spent collecting additional information from the region of interest 302. Accordingly, in the illustrated embodiment, the detector unit 310 may be controlled (e.g., by processing unit 120) to be swept or pivoted over an acquisition range 320 instead of over the entire sweep range 309 during acquisition of imaging information.

As seen in FIG. 3, the acquisition range 320 generally corresponds to edges of the region of interest 302, and is bounded by a first boundary 315 and a second boundary 316. The first boundary 315 is located at an angle α in clockwise direction from the central axis 312 (and, in the illustrated embodiment, from the center 304). The second boundary 316 is located at an angle β in a counterclockwise direction from the central axis 312 (and, in the illustrated embodiment, from the center 304). The locations of the first boundary 315 and the second boundary 316 may be determined, for example, using uptake information acquired as the detector 300 sweeps over at least a portion of the sweep range 309. For example, when a photon count exceeds a predetermined threshold (or predetermined rate of change), a boundary of the region of interest 302 (for which the uptake is higher than surrounding tissue) may be determined or identified. If the photon count is increasing past a threshold, a beginning boundary of the region of interest 302 may be determined, and if the photon count is decreasing past a threshold, an ending boundary of the region of interest 302 may be determined.

It may be noted the boundaries may not necessarily correspond to a central axis or portion of a field of view of the detector unit, but may correspond to an edge or other portion of the field of view. Further, the acquisition range 320 may be configured in various embodiments to include surrounding tissue beyond the region of interest 304 (e.g., to provide background information and/or a margin of error), and/or to omit a portion of the region of interest (e.g., to focus acquisition time even more strongly on a central portion of the region of interest that may be of particular or emphasized interest). For example, the acquisition range 320 may include an amount of background or surrounding tissue for a first phase of an acquisition period and omit background or surrounding tissue for a second phase.

Figure 4:
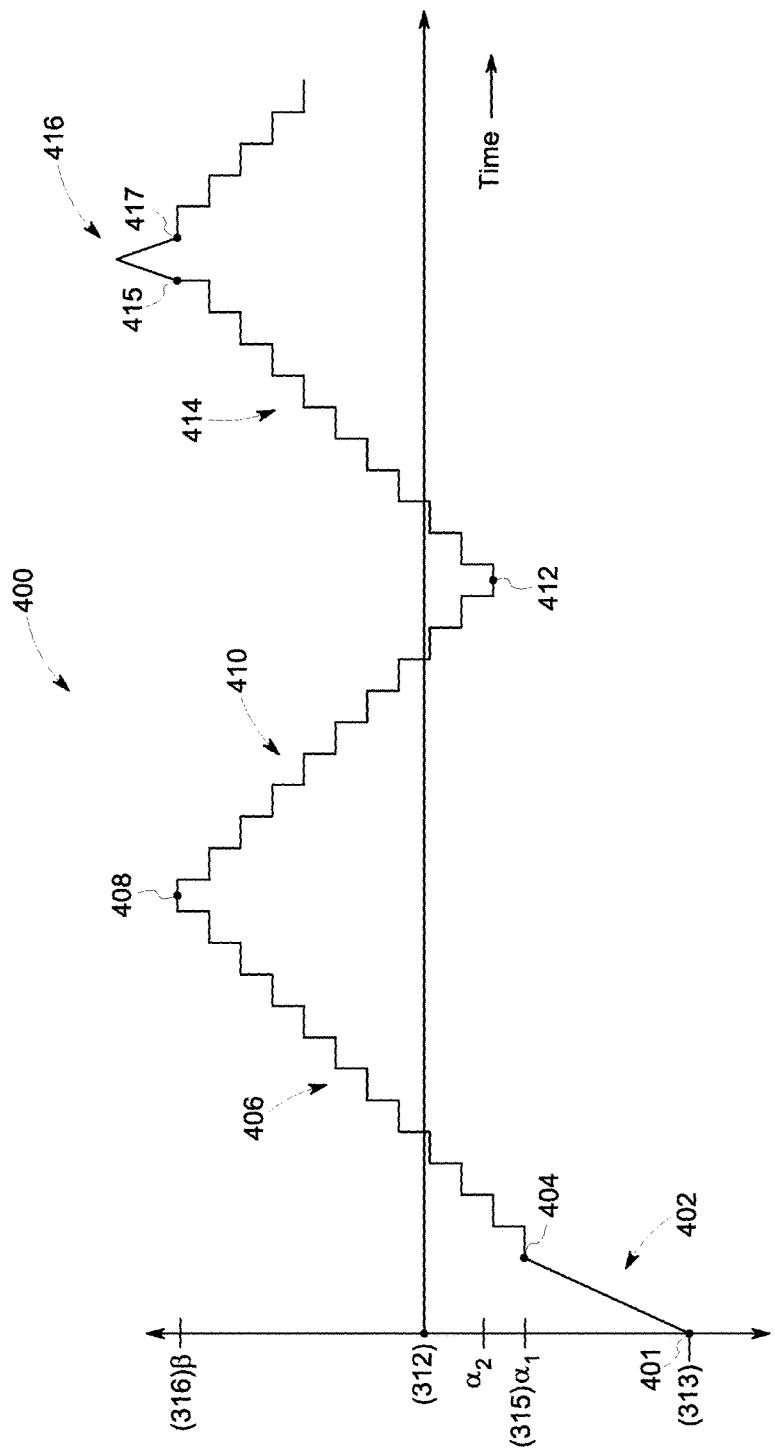
FIG. 4 illustrates an example scenario of control of the sweep of a detector unit in accordance with an embodiment.

FIG. 4 illustrates an example scenario 400 of control of the detector unit 300 during a primary image acquisition period. The detector unit 300 begins the example scenario at an initial position 401. In the illustrated embodiment the initial position 401 corresponds to the first limit 313. In some embodiments, the initial position may be located between the first limit 313 and the first boundary 315 of the acquisition range 320. For example, the initial position 401 may be estimated based on a patient size and/or type of scan to be performed, with the initial position 410 selected to be located a distance outside of an expected acquisition range. During an initial portion 402, the detector unit 300 is swept in a counterclockwise direction from the first limit 313 and toward the central axis 312. As the detector unit 300 is swept, photon counts acquired by the detector unit 300 may be sampled and analyzed. When the photon counts reach a predetermined threshold (or a rate of increase of photon counts reaches a predetermined threshold), or the photon counts otherwise satisfy a metric configured to identify an increase in counts corresponding to the region of interest 302 (or portion thereof) entering a field of view of the detector unit, a first boundary of an acquisition range (e.g., acquisition range 320) may be determined at point 404. At point 404, the detector unit 300 may be controlled to acquire imaging information of the region of interest 302. For example, the detector unit 300 may be swept at a first speed over the initial portion 402 starting from the initial position 401. However, at 404, where the first boundary of the acquisition range begins, the detector unit 300 may be swept at a second speed that is slower than the first speed. Accordingly, relatively less time is spent covering the initial portion 402 and relatively more time is spent collecting imaging information for the region of interest over the acquisition range. In the illustrated embodiment, the point 404 corresponding to the first boundary 315 is depicted as occurring at an angle α1, which may have the same value as α of FIG. 3.

Next, during portion 406, the detector unit 300 is swept counterclockwise at an acquisition speed until the second boundary 316 of the acquisition range 320 is reached. The second boundary 316 may be determined, for example, based on a decrease in the photon count satisfying a metric (e.g., threshold) corresponding to the transition from the region of interest 302 (which has a relatively high uptake and relatively high photon count) to a surrounding portion of the object 303 (which has a relatively low uptake and relatively low photon count). It may be noted that the particular metrics or thresholds used to identify the boundaries of the acquisition range 320 may be designed or selected to provide a margin of error such that the acquisition range 320 covers an amount of surrounding tissue in addition to the region of interest 302. At 408, with the second boundary 316 identified and reached, the detector unit 300 may be reversed in direction and controlled to start rotating clockwise toward the first boundary 315. Thus, the detector unit may be controlled to reverse direction responsive to a reduction in acquired photon counts.

In some embodiments, the detector unit 300 may be controlled to rotate until the already determined first boundary is met, at which point the detector unit 300 may be again reversed to rotate counterclockwise. In the illustrated embodiment, the detector unit 300 may be controlled to update at least one of the first boundary 315 or the second boundary 316 during an acquisition period. In some embodiments, for example, the first and/or second boundaries may be updated during each cycle of an acquisition period. In some embodiments, for example, the first and/or second boundaries may be updated at predetermined intervals (e.g., every 30 seconds, every minute, every other cycle, or every fifth cycle, among others). In the illustrated embodiment, during portion 410 of the example scenario, the photon counts may be collected and analyzed as the detector unit 300 rotates or sweeps toward the first boundary 315. In the illustrated embodiment, a metric corresponding to a decrease in photon count associated with a boundary of the region of interest 302 is encountered at point 412, or with the detector unit 300 rotated at an angle α2 from the central axis 312. As seen in FIG. 4, α2 differs from α1, and the first boundary accordingly may be updated to reflect a change in the uptake of the region of interest 302 over time, and/or a change in position of the region of interest 302. Accordingly, during an imaging acquisition, one or more boundaries may be updated to further focus time spent during an acquisition on portions of an object for which an increased level of uptake is present for improved image quality, while reducing time spent on portions of the object that are not of interest.

In the illustrated embodiment, the detector head reverses direction at 412 and rotates during portion 414 until the second boundary is reached (or updated) at 415. As seen in FIG. 4, after point 415, the detector head is rotated past the second boundary and then back toward the second boundary (e.g., at a faster speed than used during portion 414). The acquisition during portion 416 may be understood as occurring for a supplemental acquisition zone, and may be utilized to collect background information and/or provide a margin of error or buffer zone at the end of the acquisition range. While one supplemental acquisition zone for the second boundary is shown in the illustrated embodiment, it may be noted that a supplemental acquisition zone may be utilized in connection with the first boundary as well. Supplemental acquisition zones in various embodiments may be utilized, for example, during each back and forth sweeping cycle of a detector head, or as another example, at predetermined intervals (e.g., every 30 seconds, every minute, every other cycle, or every fifth cycle, among others). At point 417, the second boundary is again reached and the detector is swept toward the first boundary at an acquisition speed. The acquisition speed is depicted in the illustrated embodiment as occurring as a number of steps of predetermined duration. The detector head may be swept back and forth between the first and second boundaries during all or a portion of an acquisition period. For example, in some embodiments, the detector head may be swept over the sweep range or maximum range (or other range larger than the acquisition range) to collect background information over a portion of an acquisition period.

It may be noted that the control of the sweep of the detector unit 300 may be performed using only imaging information from the particular view corresponding to the detector unit 300, and using only imaging information collected by the particular detector unit 300. Information from other views or other detectors may not be utilized in various embodiments, and the use of pre-scans or associated calculations may be eliminated or reduced. It may be noted that each detector unit may have a dedicated processor (e.g., located on-board the detector unit) that performs all or a portion of the calculations required to determine the first and second boundaries for that particular detector unit.

As indicated herein, two or more of the detector units (e.g., 310(a), 310(b), 310(c) . . . ) may each be controlled using imaging information acquired by the particular detector unit (e.g., using a control scheme utilizing one or more aspects of example scenario 400). Thus, in various embodiments, the processing unit 120 (which may include individual processors disposed on-board the detectors) may independently determine corresponding acquisition ranges for at least two of the detector units 210, and independently control the at least two of the detector units over the corresponding acquisition ranges. For example, in some embodiments, all of the detector units 210 may be independently controlled to acquire imaging information over a particular acquisition range unique to a given detector unit using imaging information only from that given detector unit.

In alternate embodiments, only some of the detector units may be controlled in accordance with a control scheme incorporating at least some aspects of the the example scenario 400 (e.g., determination of boundaries of an acquisition range using dynamically acquired imaging information and control of the detector unit over the determined acquisition range), while at least one additional detector unit may be controlled to acquire imaging information over a range that is larger than an acquisition range determined based on uptake values associated only with a given detector unit. As one example, detector units 210(a), 210(c), 210(e), 210(g), 220(i), 220(k) may be controlled as disclosed herein, whereas detector units 210(b), 210(d), 210(f), 210(h), 210(j), 210(l) may be controlled to collect information over an entire sweep range or other range.

For example, as seen in FIG. 3, some detector units may be controlled to acquire information over a corresponding acquisition range 320 as discussed herein, while others are controlled to acquire information over a larger range 311. Thus, for example, multiple structures of interest having different uptake rates may be analyzed, with one or more detectors collecting information for a particular region of interest (e.g., region of interest 302), and one or more other detectors collecting information for a different and/or larger region of the object 303.

In some embodiments, the larger range 311 may coincide with the sweep range 309 or maximum available range of a detector unit. In other embodiments, the larger range 311 may be predetermined based on estimates and/or measurements of the object 303 or portions thereof. In some embodiments, the larger range 311 may be determined using a control scheme incorporating one or more aspects of the example scenario 400, but using different (e.g., lower) thresholds or metrics than used to determine the acquisition range 320.

Returning to FIG. 1, the processing unit 120 is operably coupled to the detector units 115, and acquires imaging information from at least one detector head 115, and determines boundaries of an acquisition range for the at least one detector unit 115, for example, based on photon counts encountered during a sweep or pivoting of the detector unit 115.

In various embodiments the processing unit 120 includes processing circuitry configured to perform one or more tasks, functions, or steps discussed herein. It may be noted that "processing unit" as used herein is not intended to necessarily be limited to a single processor or computer. For example, the processing unit 120 may include multiple processors, FPGA's, ASIC's and/or computers, which may be integrated in a common housing or unit, or which may be distributed among various units or housings (e.g., one or more aspects of the processing unit 120 may be disposed onboard one or more detector units, and one or more aspects of the processing unit 120 may be disposed in a separate physical unit or housing). The processing unit 120 may perform various operations in addition to the determination of acquisition range boundaries and control of detector heads. For example, the processing unit 120 may reconstruct an image using information acquired during primary image acquisition via the detector units 115. It may be noted that operations performed by the processing unit 120 (e.g., operations corresponding to process flows or methods discussed herein, or aspects thereof) may be sufficiently complex that the operations may not be performed by a human being within a reasonable time period. For example, analyzing photon counts to identify boundaries of an acquisition range, providing control signals to detector units, or the like may rely on or utilize computations that may not be completed by a person within a reasonable time period.

In the illustrated embodiment, the processing unit 120 includes a determination module 122, a control module 124, and a memory 130. It may be noted that other types, numbers, or combinations of modules may be employed in alternate embodiments, and/or various aspects of modules described herein may be utilized in connection with different modules additionally or alternatively. Generally, the various aspects of the processing unit 120 act individually or cooperatively with other aspects to perform one or more aspects of the methods, steps, or processes discussed herein.

In the illustrated embodiment, the depicted determination module 122 is configured to, responsive to received photon counts, identify boundaries of an acquisition range as disclosed herein. It may be noted that, in various embodiments, aspects of the determination module 122 may be distributed among detector units 115. For example, each detector unit may have a dedicated determination module disposed in the head 116 of the detector unit 115. It may be noted that in various embodiments the determination of boundaries of an acquisition range of a given detector unit is determined using imaging information only from the given detector unit, or without using imaging information from any other detector unit.

The depicted control module 124 is configured to, responsive to boundaries determined by the determination module, control one or more detector heads 116 to sweep over a corresponding acquisition range. For example, responsive to an increased photon count (e.g., a photon count satisfying a predetermined metric corresponding to reaching or approaching the beginning of a range covering a region of interest), the control module 124 may control a detector head to continue sweeping in an initial direction, but at a slower speed than an initial speed utilized before the increased photon count. As another example, responsive to a decreased photon count (e.g., a photon count satisfying a predetermined metric corresponding to reaching or approaching the end of a range covering a region of interest), the control module 124 may control a detector head to reverse direction of sweep. It may be noted that, in various embodiments, aspects of the control module 124 may be distributed among detector units 115. For example, each detector unit may have a dedicated control module disposed in the head 116 of the detector unit 115.

The memory 130 may include one or more computer readable storage media. The memory 130, for example, may store information describing previously determined boundaries of acquisition ranges, predetermined thresholds or other metrics utilized for determining boundaries of acquisition ranges, parameters to be utilized during performance of a scan (e.g., speed of rotation for acquisition range, speed of rotation for supplement zone, time or total count value over which an acquisition is to be performed), or the like. Further, the process flows and/or flowcharts discussed herein (or aspects thereof) may represent one or more sets of instructions that are stored in the memory 130 for direction of operations of the imaging system 100.

It may be noted that while the processing unit 120 is depicted schematically in FIG. 1 as separate from the detector units 115, in various embodiments, one or more aspects of the processing unit 120 may be shared with the detector units 115, associated with the detector units 115, and/or disposed onboard the detector units 115. For example, in some embodiments, at least a portion of the processing unit 120 is integrated with at least one of the detector units 115. In various embodiments, at least a portion of the processing unit 120 includes at least one application specific integrated circuit (ASIC) or field programmable gate array (FPGA) that is disposed onboard or integrated with at least one of the detector units.

Figure 5:
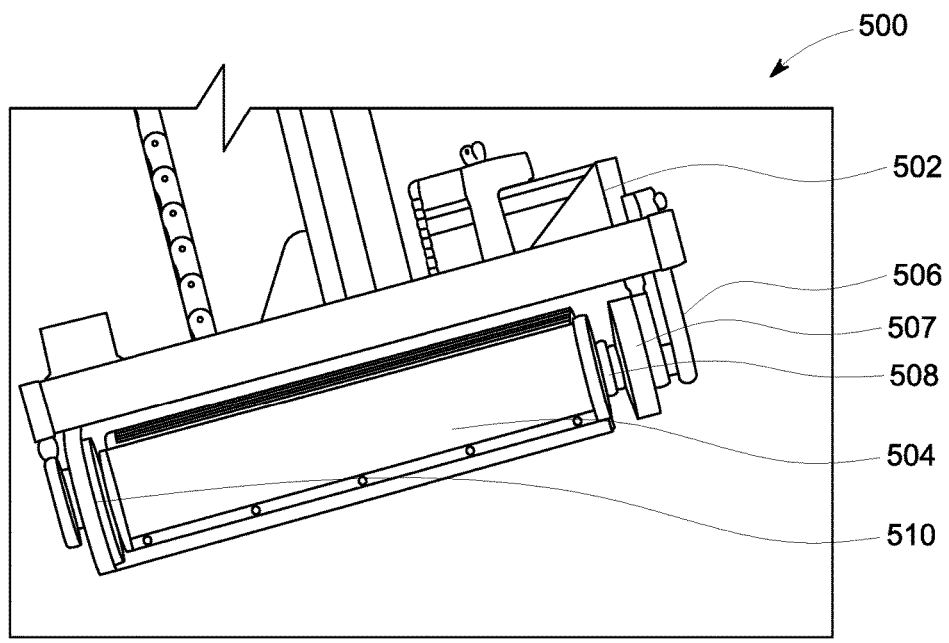
FIG. 5 provides a schematic view of a detector head in accordance with an embodiment.
Figure 6:
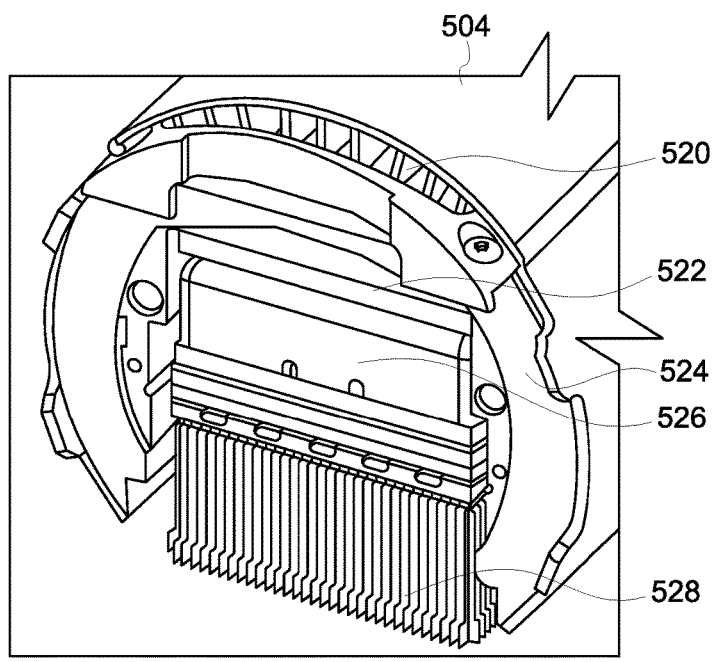
FIG. 6 shows a sectional view of the detector head of FIG. 5.

FIG. 5 is a schematic view of an example detector head 500 formed in accordance with various embodiments, and FIG. 6 is a sectional view of the detector head 500. As seen in FIG. 5, the detector head 500 includes a stepper motor 502 that may be utilized to pivot a detector column 504. It may be noted that motors other than stepper motors may be used in various embodiments. It may also be noted that the steps depicted in FIG. 4, for example, do not necessarily correspond to the elemental steps of the stepper motor 502. It may further be noted that continuous motion (e.g., of varying speeds) may be utilized in embodiments of the invention, instead of the staircase type motion depicted in FIG. 4. Generally, "step and shoot" motion may be employed in various embodiments. In step and shoot motion, the detector is rapidly pivoted, and then remains stationary during data collection. Step and shoot motion may be utilized in various embodiments to eliminate or reduce power transients and/or other electronic noise associated with activation of electrical motors. Use of step and shoot motion may also be utilized to eliminate orientation uncertainties associated with each collected photon. However, it may be noted that, in various embodiments, with fine orientation encoders, and frequent sampling of the orientation encoders, detector aiming may be associated with each detected photon to sufficient accuracy even if the detectors are continuously pivoting during data acquisition. The detector column 504, for example, may include a shield, a processing board, a detector (e.g., a CZT detector) and a collimator. The detector head 500 also includes a gear 506 coupling the stepper motor to the column 504, as well as a slip ring 507 (configured to allow for transfer of signals between the rotating detector column 504 and non-rotating components) and a multiplex board 508. In the illustrated embodiment, the detector head 500 also includes an air channel 510 configured to provide cooling to components of the detector head 500. As seen in FIG. 6, the detector column 504 includes a heat sink 520, a printed circuit board 522 (which may incorporate one or more aspects of the processing unit 120), a lead shielding 524, a CZT detector module 526, and collimator 528 that is registered to the CZT detector module 526 in the illustrated embodiment. Additional details and discussion regarding detector heads is provided in U.S. patent application Ser. No. 14/671,039, entitled "Reduced Airborne Contamination Detector Heads," filed Mar. 27, 2015, the subject matter of which is hereby incorporated by reference in its entirety.

Figure 7:
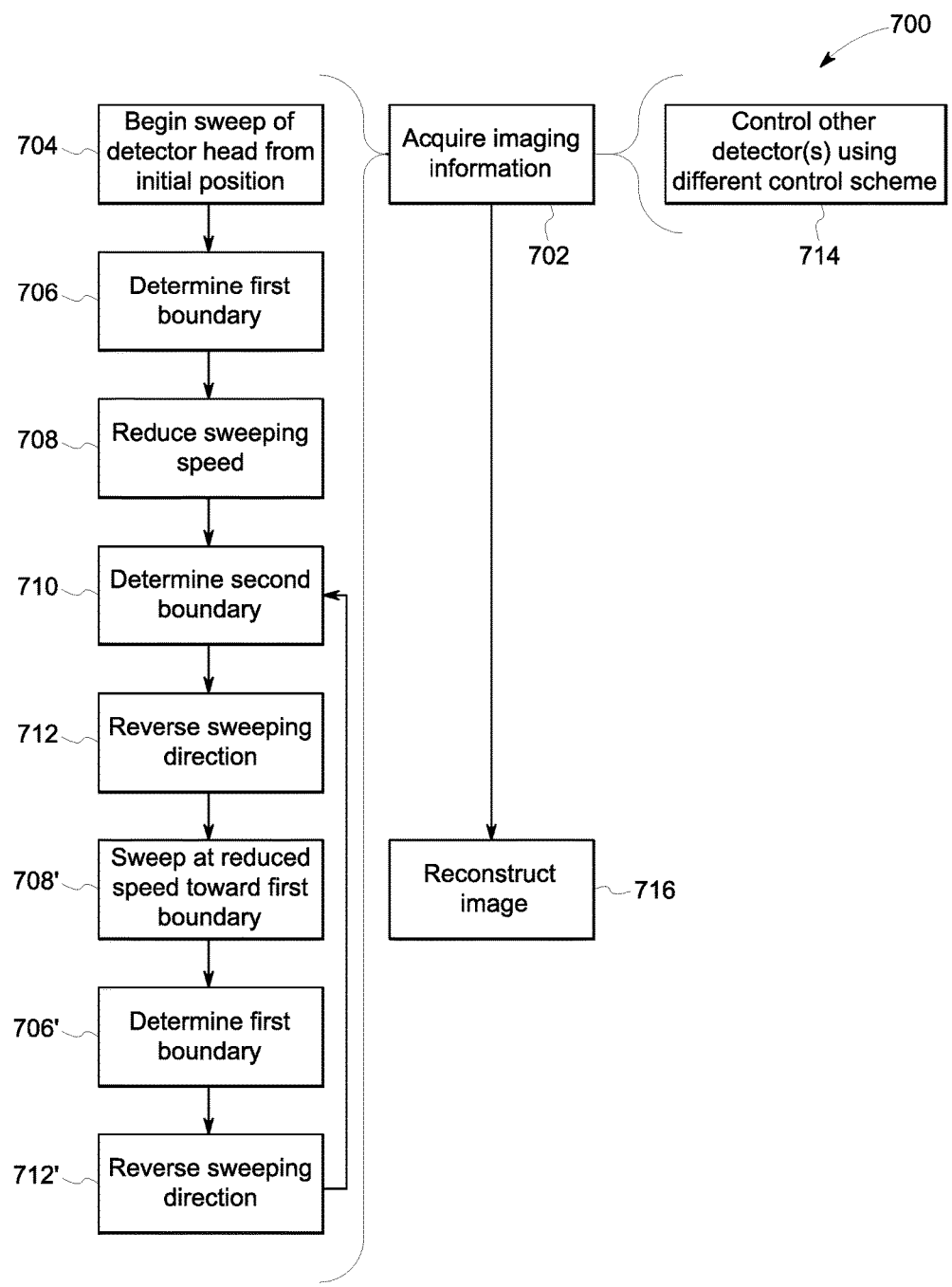
FIG. 7 shows a flowchart of a method, according to an embodiment.

FIG. 7 provides a flowchart of a method 700 for controlling detector heads of a multi-head imaging system in accordance with various embodiments. The method 700, for example, may employ or be performed by structures or aspects of various embodiments (e.g., systems and/or methods and/or process flows) discussed herein. In various embodiments, certain steps may be omitted or added, certain steps may be combined, certain steps may be performed concurrently, certain steps may be split into multiple steps, certain steps may be performed in a different order, or certain steps or series of steps may be re-performed in an iterative fashion. In various embodiments, portions, aspects, and/or variations of the method 700 may be able to be used as one or more algorithms to direct hardware (e.g., one or more aspects of the processing unit 120) to perform one or more operations described herein.

At 702, imaging information is acquired. For example, in various embodiments, imaging information may be acquired as a primary imaging acquisition that will be used to reconstruct an image to be used for diagnostic purposes. The imaging information for the depicted embodiment is acquired with plural detector units mounted to a gantry defining a bore configured to accept an object to be imaged. As discussed herein, each detector unit defines a corresponding view oriented toward a center of the bore, with each detector unit configured to acquire the imaging information over a sweep range corresponding to the view of the given detector unit.

At 704, as part of the acquisition of imaging information in the illustrated embodiment, at least one of the detector units may begin a sweep from an initial point toward a region of interest. The initial point in some embodiments may be at a limit of a maximum sweep range of the detector unit. In other embodiments, the initial point may be determined based on a priori knowledge, such as a size of a patient and/or a type of scan being performed. The detector unit may be swept at a relatively high speed as it is swept from the initial point toward the region of interest.

At 706, a first boundary of an acquisition range for at least one of the detector units is determined. The acquisition range is smaller than the sweep range, thereby focusing additional acquisition time on the region of interest, improving image quality and/or reducing an overall or total acquisition time. The first boundary, for example, may correspond to a transition within the field of view of the rotating detector unit from tissue surrounding a region of interest to at least a portion of the region of interest itself being disposed within the field of view. For example, the first boundary may correspond to a position at which one-half (or other fraction) of the region of interest is within the field of view of the detector unit. As another example, the first boundary may be defined when the edge of the ROI is nearing the end of the FOV, while at least a substantial part of the FOV is viewing the ROI. In various embodiments, a substantial part of the FOV may be understood as, for example, over 50% of the area defined by the FOV, over 75% of the area defined by the FOV, or over 90% of the area defined by the FOV, as examples. For example, as seen in FIG. 3, an FOV 321 taken at the first boundary 315 corresponds to an image view 323 shown in FIG. 3. In the image view 323, an edge 324 between the ROI 302 and surrounding tissue 322 is located near an edge of the image view 323 or FOV 321. In the depicted embodiment, the first boundary is dynamically determined during the primary image acquisition. The first boundary corresponds to, and may be determined based on, an uptake value of the object to be imaged. For example, the uptake value associated with the first boundary is larger than the uptake value for tissue surrounding the region of interest. The first boundary in various embodiments is determined based on a change of photon counts acquired by the detector unit. For example, the first boundary may be determined when the photon counts acquired by the detector unit increase to a level satisfying a predetermined threshold or metric.

At 708, responsive to the determination and identification of the first boundary, the speed of the sweeping or pivoting of the detector unit is reduced from an initial speed to an acquisition speed, with the detector unit still sweeping in the same direction.

At 710, as the detector unit continues to sweep in the initial direction, a second boundary of the acquisition range is determined. The second boundary, for example, may correspond to a transition within the field of view of the rotating detector unit from the region of interest itself (or a portion thereof) being disposed within the field of view to tissue surrounding the region of interest being disposed within the field of view. For example, the second boundary may correspond to a position at which one-half (or other fraction) of the region of interest is within the field of view of the detector unit. In the depicted embodiment, the second boundary is dynamically determined during the primary image acquisition. The second boundary corresponds to, and may be determined based on, an uptake value of the object to be imaged. The second boundary in various embodiments is determined based on a change of photon counts acquired by the detector unit. For example, the second boundary may be determined when the photon counts acquired by the detector unit decrease to a level satisfying a predetermined threshold or metric.

At 712, responsive to the determination and identification of the second boundary, the direction of the sweeping or pivoting of the detector unit is reversed, with the detector unit swept toward the first boundary. This is schematically depicted in FIG. 7 by the optional steps 708' (sweeping at reduced speed toward the first boundary), 706' (determining the first boundary), and 712' (again reversing the sweeping direction until the second boundary is determined or reached at 710). It may be noted that in some embodiments, at 706', the previously determined first boundary may be utilized as a point at which the sweeping is reversed.

Figure 8:
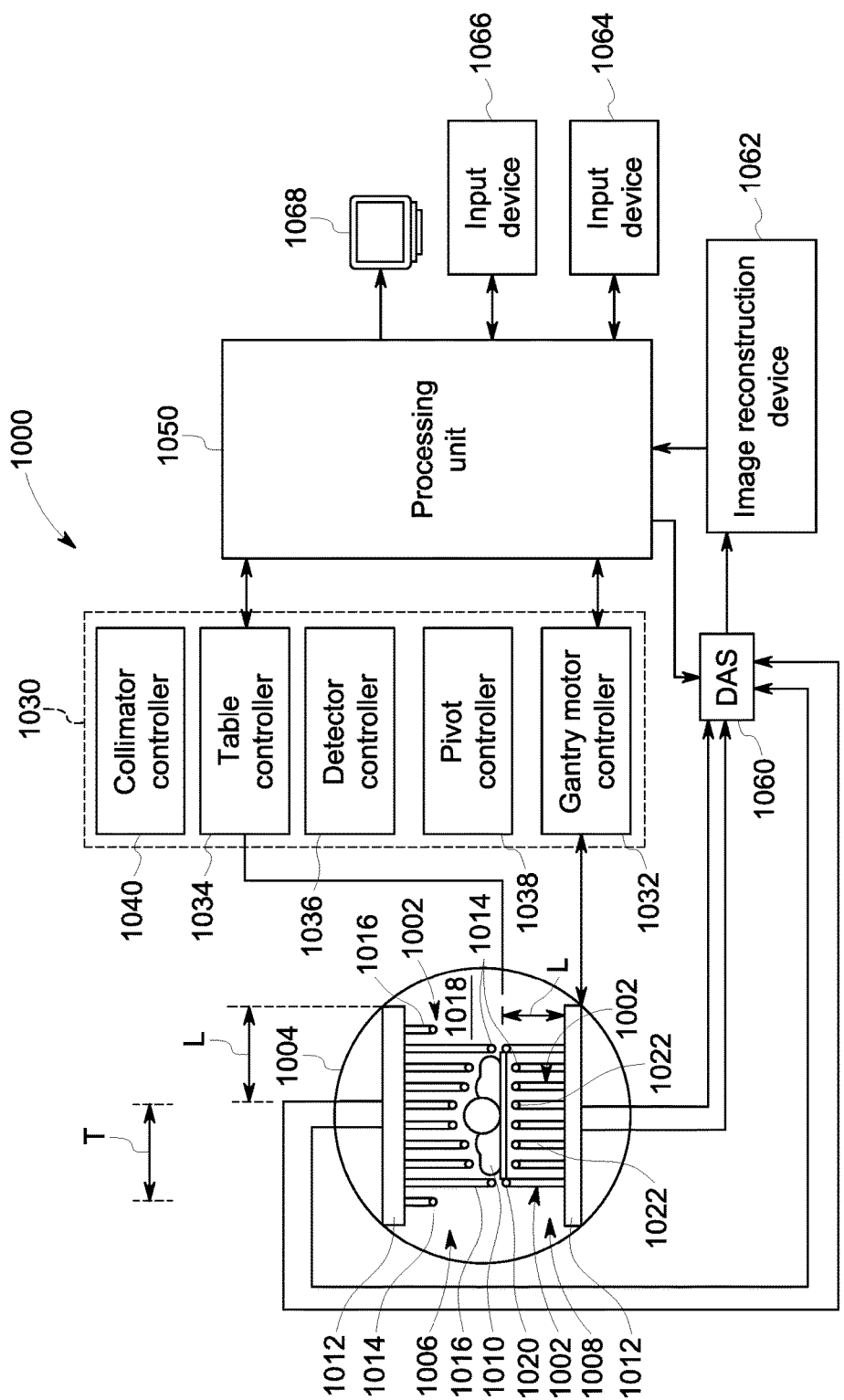
FIG. 8 shows a schematic view of an imaging system, according to an embodiment.

It may be noted that the detector unit may be swept back and forth between the first and second boundaries until an acquisition period is completed. The acquisition period may have a duration corresponding to an amount of time or a number of photon counts sufficient to provide a desired resolution or image quality. As discussed herein, the first and second boundaries may be updated during the image acquisition in various embodiments. It may further be noted that multiple detectors may be independently controlled, for example using one or more aspects of steps 704-712. Further, in some embodiments, one or more detectors may be controlled pursuant to steps 704-712, while one or more other detectors are controlled pursuant to a different control scheme, as indicated at 714. It should be noted that acquiring imaging information 702 may be concurrent to steps 704-712'. Optionally, when the pivoting and sweeping represented by the chain of steps 712' is completed (or a given number of iterations of the chain of steps is completed), a gantry (e.g., gantry 110) may rotate (or shift as gantry 1004 of FIG. 8 is configured to shift) to move the detector heads slightly, and the chain of steps 704-712' may be repeated while the detector heads are in different positions with respect to the patient. For example, the one or more other detectors may acquire imaging information over a range larger than an acquisition range corresponding to the region of interest, for example, to acquire additional background information and/or to acquire information of a different or additional region of interest. The one or more other detectors may be configured to acquire imaging information corresponding to one or more additional regions of interest that corresponds to uptake of a different radiopharmaceutical than the region of interest corresponding to the acquisition range of steps 704-712.

At 716, when the primary acquisition duration has been satisfied, an image is reconstructed using imaging information acquired during the primary acquisition. It may be noted that the imaging information used to dynamically adjust the sweeping of at least some of the detector units is also used to reconstruct the image.

In some embodiments, a detector head (or detector heads) may start the imaging data acquisition with an FOV of one or more heads pointing directly to the center of the bore, or to another position at which the FOV is entirely viewing the ROI. When aimed at the center of the bore, the ROI is within the FOV, and it is most likely that the narrow FOV is entirely viewing the ROI. The detector head (or heads) may then pivot at reduced speed until the second boundary is encountered and determined. The method may then continue as discussed herein, following steps 712, 708', 706' 712', 710 and so on. Alternatively, a detector head (or heads) may begin being pointed at the center of the bore or other position at which the FOV is entirely viewing the ROI, and rotate or pivot toward the first boundary.

In some embodiments, it may be beneficial to reconstruct the entire object 303, with the ROI 302 reconstructed at an enhanced resolution and/or at an enhanced accuracy. Accordingly, more dwell time may be spent while the FOV is aimed at the ROI, and less dwell time while the FOV is aimed at parts of the object 303 (e.g., surrounding tissue 322) which are outside of the ROI 302. Accordingly, in some embodiments, two additional boundaries may be determined: first and second object boundaries at the two ends of the larger range 311 or other range that includes portions of the surrounding tissue 322. Sweeping of a detector head may then proceed at a fast or intermediate rate between first object boundary and first boundary (e.g., while viewing the surrounding tissue 322), with sweeping of the detector head proceeding at a reduced rate between the first and second boundaries (e.g., while viewing the ROI 302), and again at a fast or intermediate rate between the second object boundary and the second boundary (e.g., while viewing the surrounding tissue 322).

In various embodiments, pivoting speed may remain slow, however, for N sweeps between the first and second boundaries, while there are M sweeps between the first object boundary and second object boundary. Thus, while the range between the first and second boundaries corresponding to the ROI is swept N+M times, the range outside the ROI is swept only M times.

Similarly, the sweeping sequence, in some embodiments may be: from the first object boundary to the second boundary, then reverse direction and sweep to the first boundary, then reverse direction and sweep to the second object boundary, and then reverse the sequence. In this way, the ROI is sampled twice as long as the non-ROI parts of the object.

It may be noted that, usually, the radioisotope concentration in the non-ROI parts of the object is reduced compared to the radioisotope concentration in the ROI parts of the object. However, this may not always be the case, as voids or parts of the body having less affinity, and/or defects in parts of body, may be the subject of the imaging, and thus included in the ROI. It may be noted that the radioisotope concentration in the non-ROI parts of the object may generally be high enough to distinguish the non-ROT parts of the object from regions outside the object where no radiation is emitted at all. Thus, the determination of the object boundaries is generally possible (e.g., by utilizing a lower threshold for determination of the first and second object boundaries compared to the first and second boundaries corresponding to the ROI).

The embodiments described above and illustrated by FIGS. 1-7 may be implemented in medical imaging systems, such as, for example, SPECT, SPECT-CT, PET and PET-CT. Various methods and/or systems (and/or aspects thereof) described herein may be implemented using a medical imaging system. For example, FIG. 8 is a schematic illustration of a NM imaging system 1000 having a plurality of imaging detector head assemblies mounted on a gantry (which may be mounted, for example, in rows, in an iris shape, or other configurations, such as a configuration in which the movable detector carriers 1016 are aligned radially toward the patient-body 1010). It should be noted that the arrangement of FIG. 8 is provided by way of example for illustrative purposes, and that other arrangements (e.g., detector arrangements) may be employed in various embodiments. In the illustrated example, a plurality of imaging detectors 1002 are mounted to a gantry 1004. In the illustrated embodiment, the imaging detectors 1002 are configured as two separate detector arrays 1006 and 1008 coupled to the gantry 1004 above and below a subject 1010 (e.g., a patient), as viewed in FIG. 8. The detector arrays 1006 and 1008 may be coupled directly to the gantry 1004, or may be coupled via support members 1012 to the gantry 1004 to allow movement of the entire arrays 1006 and/or 1008 relative to the gantry 1004 (e.g., transverse translating movement in the left or right direction as viewed by arrow T in FIG. 8). Additionally, each of the imaging detectors 1002 includes a detector unit 1014, at least some of which are mounted to a movable detector carrier 1016 (e.g., a support arm or actuator that may be driven by a motor to cause movement thereof) that extends from the gantry 1004. In some embodiments, the detector carriers 1016 allow movement of the detector units 1014 towards and away from the subject 1010, such as linearly. Thus, in the illustrated embodiment the detector arrays 1006 and 1008 are mounted in parallel above and below the subject 1010 and allow linear movement of the detector units 1014 in one direction (indicated by the arrow L), illustrated as perpendicular to the support member 1012 (that are coupled generally horizontally on the gantry 1004). However, other configurations and orientations are possible as described herein. It should be noted that the movable detector carrier 1016 may be any type of support that allows movement of the detector units 1014 relative to the support member 1012 and/or gantry 1004, which in various embodiments allows the detector units 1014 to move linearly towards and away from the support member 1012.

Each of the imaging detectors 1002 in various embodiments is smaller than a conventional whole body or general purpose imaging detector. A conventional imaging detector may be large enough to image most or all of a width of a patient's body at one time and may have a diameter or a larger dimension of approximately 50 cm or more. In contrast, each of the imaging detectors 1002 may include one or more detector units 1014 coupled to a respective detector carrier 1016 and having dimensions of, for example, 4 cm to 20 cm and may be formed of Cadmium Zinc Telluride (CZT) tiles or modules. For example, each of the detector units 1014 may be 8×8 cm in size and be composed of a plurality of CZT pixelated modules (not shown). For example, each module may be 4×4 cm in size and have 16×16=256 pixels (pixelated anodes). In some embodiments, each detector unit 1014 includes a plurality of modules, such as an array of 1×7 modules. However, different configurations and array sizes are contemplated including, for example, detector units 1014 having multiple rows of modules.

It should be understood that the imaging detectors 1002 may be different sizes and/or shapes with respect to each other, such as square, rectangular, circular or other shape. An actual field of view (FOV) of each of the imaging detectors 1002 may be directly proportional to the size and shape of the respective imaging detector.

The gantry 1004 may be formed with an aperture 1018 (e.g., opening or bore) therethrough as illustrated. A patient table 1020, such as a patient bed, is configured with a support mechanism (not shown) to support and carry the subject 1010 in one or more of a plurality of viewing positions within the aperture 1018 and relative to the imaging detectors 1002. Alternatively, the gantry 1004 may comprise a plurality of gantry segments (not shown), each of which may independently move a support member 1012 or one or more of the imaging detectors 1002.

The gantry 1004 may also be configured in other shapes, such as a "C", "H" and "L", for example, and may be rotatable about the subject 1010. For example, the gantry 1004 may be formed as a closed ring or circle, or as an open arc or arch which allows the subject 1010 to be easily accessed while imaging and facilitates loading and unloading of the subject 1010, as well as reducing claustrophobia in some subjects 1010.

Additional imaging detectors (not shown) may be positioned to form rows of detector arrays or an arc or ring around the subject 1010. By positioning multiple imaging detectors 1002 at multiple positions with respect to the subject 1010, such as along an imaging axis (e.g., head to toe direction of the subject 1010) image data specific for a larger FOV may be acquired more quickly.

Each of the imaging detectors 1002 has a radiation detection face, which is directed towards the subject 1010 or a region of interest within the subject.

The collimators 1022 (and detectors) in FIG. 8 are depicted for ease of illustration as single collimators in each detector head. Optionally, for embodiments employing one or more parallel-hole collimators, multi-bore collimators may be constructed to be registered with pixels of the detector units 1014, which in one embodiment are CZT detectors. However, other materials may be used. Registered collimation may improve spatial resolution by forcing photons going through one bore to be collected primarily by one pixel. Additionally, registered collimation may improve sensitivity and energy response of pixelated detectors as detector area near the edges of a pixel or in-between two adjacent pixels may have reduced sensitivity or decreased energy resolution or other performance degradation. Having collimator septa directly above the edges of pixels reduces the chance of a photon impinging at these degraded-performance locations, without decreasing the overall probability of a photon passing through the collimator.

A controller unit 1030 may control the movement and positioning of the patient table 1020, imaging detectors 1002 (which may be configured as one or more arms), gantry 1004 and/or the collimators 1022 (that move with the imaging detectors 1002 in various embodiments, being coupled thereto). A range of motion before or during an acquisition, or between different image acquisitions, is set to maintain the actual FOV of each of the imaging detectors 1002 directed, for example, towards or "aimed at" a particular area or region of the subject 1010 or along the entire subject 1010. The motion may be a combined or complex motion in multiple directions simultaneously, concurrently, or sequentially.

The controller unit 1030 may have a gantry motor controller 1032, table controller 1034, detector controller 1036, pivot controller 1038, and collimator controller 1040. The controllers 1030, 1032, 1034, 1036, 1038, 1040 may be automatically commanded by a processing unit 1050, manually controlled by an operator, or a combination thereof. The gantry motor controller 1032 may move the imaging detectors 1002 with respect to the subject 1010, for example, individually, in segments or subsets, or simultaneously in a fixed relationship to one another. For example, in some embodiments, the gantry controller 1032 may cause the imaging detectors 1002 and/or support members 1012 to move relative to or rotate about the subject 1010, which may include motion of less than or up to 180 degrees (or more).

The table controller 1034 may move the patient table 1020 to position the subject 1010 relative to the imaging detectors 1002. The patient table 1020 may be moved in up-down directions, in-out directions, and right-left directions, for example. The detector controller 1036 may control movement of each of the imaging detectors 1002 to move together as a group or individually. The detector controller 1036 also may control movement of the imaging detectors 1002 in some embodiments to move closer to and farther from a surface of the subject 1010, such as by controlling translating movement of the detector carriers 1016 linearly towards or away from the subject 1010 (e.g., sliding or telescoping movement). Optionally, the detector controller 1036 may control movement of the detector carriers 1016 to allow movement of the detector array 1006 or 1008. For example, the detector controller 1036 may control lateral movement of the detector carriers 1016 illustrated by the T arrow (and shown as left and right as viewed in FIG. 10). In various embodiments, the detector controller 1036 may control the detector carriers 1016 or the support members 1012 to move in different lateral directions. Detector controller 1036 may control the swiveling motion of detectors 1002 together with their collimators 1022. In some embodiments, detectors 1002 and collimators 1022 may swivel or rotate around an axis.

The pivot controller 1038 may control pivoting or rotating movement of the detector units 1014 at ends of the detector carriers 1016 and/or pivoting or rotating movement of the detector carrier 1016. For example, one or more of the detector units 1014 or detector carriers 1016 may be rotated about at least one axis to view the subject 1010 from a plurality of angular orientations to acquire, for example, 3D image data in a 3D SPECT or 3D imaging mode of operation. The collimator controller 1040 may adjust a position of an adjustable collimator, such as a collimator with adjustable strips (or vanes) or adjustable pinhole(s).

It should be noted that motion of one or more imaging detectors 1002 may be in directions other than strictly axially or radially, and motions in several motion directions may be used in various embodiment. Therefore, the term "motion controller" may be used to indicate a collective name for all motion controllers. It should be noted that the various controllers may be combined, for example, the detector controller 1036 and pivot controller 1038 may be combined to provide the different movements described herein.

Prior to acquiring an image of the subject 1010 or a portion of the subject 1010, the imaging detectors 1002, gantry 1004, patient table 1020 and/or collimators 1022 may be adjusted, such as to first or initial imaging positions, as well as subsequent imaging positions. The imaging detectors 1002 may each be positioned to image a portion of the subject 1010. Alternatively, for example in a case of a small size subject 1010, one or more of the imaging detectors 1002 may not be used to acquire data, such as the imaging detectors 1002 at ends of the detector arrays 1006 and 1008, which as illustrated in FIG. 8 are in a retracted position away from the subject 1010. Positioning may be accomplished manually by the operator and/or automatically, which may include using, for example, image information such as other images acquired before the current acquisition, such as by another imaging modality such as X-ray Computed Tomography (CT), MRI, X-Ray, PET or ultrasound. In some embodiments, the additional information for positioning, such as the other images, may be acquired by the same system, such as in a hybrid system (e.g., a SPECT/CT system). Additionally, the detector units 1014 may be configured to acquire non-NM data, such as x-ray CT data. In some embodiments, a multi-modality imaging system may be provided, for example, to allow performing NM or SPECT imaging, as well as x-ray CT imaging, which may include a dual-modality or gantry design as described in more detail herein.

After the imaging detectors 1002, gantry 1004, patient table 1020, and/or collimators 1022 are positioned, one or more images, such as three-dimensional (3D) SPECT images are acquired using one or more of the imaging detectors 1002, which may include using a combined motion that reduces or minimizes spacing between detector units 1014. The image data acquired by each imaging detector 1002 may be combined and reconstructed into a composite image or 3D images in various embodiments.

In one embodiment, at least one of detector arrays 1006 and/or 1008, gantry 1004, patient table 1020, and/or collimators 1022 are moved after being initially positioned, which includes individual movement of one or more of the detector units 1014 (e.g., combined lateral and pivoting movement) together with the swiveling motion of detectors 1002. For example, at least one of detector arrays 1006 and/or 1008 may be moved laterally while pivoted. Thus, in various embodiments, a plurality of small sized detectors, such as the detector units 1014 may be used for 3D imaging, such as when moving or sweeping the detector units 1014 in combination with other movements.

In various embodiments, a data acquisition system (DAS) 1060 receives electrical signal data produced by the imaging detectors 1002 and converts this data into digital signals for subsequent processing. However, in various embodiments, digital signals are generated by the imaging detectors 1002. An image reconstruction device 1062 (which may be a processing device or computer) and a data storage device 1064 may be provided in addition to the processing unit 1050. It should be noted that one or more functions related to one or more of data acquisition, motion control, data processing and image reconstruction may be accomplished through hardware, software and/or by shared processing resources, which may be located within or near the imaging system 1000, or may be located remotely. Additionally, a user input device 1066 may be provided to receive user inputs (e.g., control commands), as well as a display 1068 for displaying images. DAS 1060 receives the acquired images from detectors 1002 together with the corresponding lateral, vertical, rotational and swiveling coordinates of gantry 1004, support members 1012, detector units 1014, detector carriers 1016, and detectors 1002 for accurate reconstruction of an image including 3D images and their slices.

It should be noted that the particular arrangement of components (e.g., the number, types, placement, or the like) of the illustrated embodiments may be modified in various alternate embodiments. For example, in various embodiments, different numbers of a given module or unit may be employed, a different type or types of a given module or unit may be employed, a number of modules or units (or aspects thereof) may be combined, a given module or unit may be divided into plural modules (or sub-modules) or units (or sub-units), one or more aspects of one or more modules may be shared between modules, a given module or unit may be added, or a given module or unit may be omitted.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a processing unit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

As used herein, the term "computer," "processor," or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer," "processor," or "module."

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" may include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, the embodiments are by no means limiting and are exemplary embodiments. Many other embodiments will be apparent to those of skill in the art upon reviewing the above description. The scope of the various embodiments should, therefore, be determined with reference to the appended claims, along with the full scope of equivalents to which such claims are entitled.

In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. A nuclear medicine (NM) multi-head imaging system comprising:
    a gantry defining a bore configured to accept an object to be imaged;
    plural detector units mounted to the gantry, each detector unit defining a corresponding view oriented toward a center of the bore and configured to acquire imaging information over a sweep range corresponding to the corresponding view, the detector units configured to pivot to define the corresponding sweep ranges; and
    at least one processor operably coupled to at least one of the detector units, the at least one processor configured to:
        control at least one of the detector units to sweep over an initial range during a primary image acquisition configured to obtain information for reconstructing an image;
        dynamically determine, during the primary image acquisition, at least one boundary of an angular range of an acquisition range over which the at least one of the detector units is to be swept, wherein the at least one boundary of the angular range of the acquisition range is dynamically determined based on photon counts crossing a threshold during sweeping of the at least one of the detector units, wherein the acquisition range is over a smaller angular range than the initial range, the acquisition range corresponding to an uptake value of the object to be imaged for the at least one of the detector units, and
        control, during the primary acquisition configured to obtain information for reconstructing the image, the at least one detector unit to sweep over the acquisition range to acquire imaging information over the acquisition range.

2. The system of claim 1, wherein the at least one processor is configured to independently determine corresponding acquisition ranges for at least two of the detector units and independently control the at least two of the detector units over the corresponding acquisition ranges.

3. The system of claim 1, wherein the system comprises at least one additional detector unit in addition to the at least one of the detector units, wherein the at least one processor is configured to control the at least one additional detector unit to acquire imaging information over a range that is larger than a corresponding acquisition range defined by the uptake value of the object to be imaged for the additional detector unit.

4. The system of claim 1, wherein the at least one processor is configured to update the at least one boundary of the acquisition range during the primary image acquisition.

5. The system of claim 1, wherein the at least one processor is configured to determine the at least one boundary of the acquisition range based on a change of photon counts acquired by the at least one detector unit.

6. The system of claim 5, wherein the at least one processor is configured to control the at least one detector unit to reverse a direction of rotation when a reduction in the photon counts acquired by the at least one detector unit satisfies a metric corresponding to a transition from a region of interest to a surrounding portion of the object.

7. The system of claim 1, wherein the at least one processor is configured to control the at least one detector unit at a first speed from an initial position to a first boundary of the acquisition range, and at a second speed over the acquisition range, wherein the first speed is faster than the second speed.

8. The system of claim 1, wherein the detector unit comprises a detector and a collimator registered to the detector disposed in a detector head, wherein the detector head is configured to pivot about an axis over the sweep range.

9. A method comprising:
acquiring imaging information with plural detector units mounted to a gantry defining a bore configured to accept an object to be imaged, each detector unit defining a corresponding view oriented toward a center of the bore and configured to acquire the imaging information over a sweep range corresponding to the corresponding view, the detector units configured to pivot to define the corresponding sweep ranges;
controlling at least one of the detector units to sweep over an initial range during a primary image acquisition configured to obtain information for reconstructing an image;
dynamically determining, during the primary image acquisition, at least one boundary of an angular range of an acquisition range over which the at least one of the detector units is to be swept, wherein the at least one boundary of the angular range of the acquisition range is dynamically determined based on photon counts crossing a threshold during sweeping of the at least one of the detector units, wherein the acquisition range is over a smaller angular range than the initial range, the acquisition range corresponding to an uptake value of the object to be imaged for at least one of the detector units; and
controlling, during the primary acquisition configured to obtain information for reconstructing the image, the at least one detector unit to sweep over the acquisition range to acquire imaging information over the acquisition range.

10. The method of claim 9, further comprising independently determining corresponding acquisition ranges for at least two of the detector units and independently controlling the at least two of the detector units over the corresponding acquisition ranges.

11. The method of claim 9, wherein the system comprises at least one additional detector unit in addition to the at least one detector unit, the method further comprising controlling the at least one additional detector unit to acquire imaging information over a range that is larger than a corresponding acquisition range defined by the uptake value of the object to be imaged for the additional detector unit.

12. The method of claim 9, further comprising updating the at least one boundary of the acquisition range during the primary image acquisition.

13. The method of claim 9, wherein determining the at least one boundary of the acquisition range is performed based on a change of photon counts acquired by the at least one detector unit.

14. The method of claim 13, further comprising controlling the at least one detector unit to reverse a direction of rotation when a reduction in the photon counts acquired by the at least one detector unit satisfies a metric corresponding to a transition from a region of interest to a surrounding portion of the object.

15. The method of claim 9, further comprising controlling the at least one detector unit at a first speed from an initial position to a first boundary of the acquisition range, and at a second speed over the acquisition range, wherein the first speed is faster than the second speed.

16. A tangible and non-transitory computer readable medium comprising one or more software modules configured to direct one or more processors to:
acquire imaging information with plural detector units mounted to a gantry defining a bore configured to accept an object to be imaged, each detector unit defining a corresponding view oriented toward a center of the bore and configured to acquire the imaging information over a sweep range corresponding to the corresponding view, the detector units configured to pivot to define the corresponding sweep ranges;
control at least one of the detector units to sweep over an initial range during a primary image acquisition configured to obtain information for reconstructing an image;
dynamically determine, during the primary image acquisition, at least one boundary of an angular range of an an acquisition range over which the at least one of the detector units is to be swept, wherein the at least one boundary of the angular range of the acquisition range is dynamically determined based on photon counts crossing a threshold during sweeping of the at least one of the detector units, wherein the acquisition range is over a smaller angular range than the initial range, the acquisition range corresponding to an uptake value of the object to be imaged for at least one of the detector units; and
control, during the primary acquisition configured to obtain information for reconstructing the image, the at least one detector unit to sweep over the acquisition range to acquire imaging information over the acquisition range.

17. The tangible and non-transitory computer readable medium of claim 16, wherein the one or more software modules are further configured to direct the one or more processors to independently determine corresponding acquisition ranges for at least two of the detector units and independently control the at least two of the detector units over the corresponding acquisition ranges.

18. The tangible and non-transitory computer readable medium of claim 16, wherein the at least one detector units comprise the system comprises at least one additional detector unit in addition to the at least one of the detector units, wherein the one or more software modules are further configured to direct the one or more processors to control the at least one additional detector unit to acquire imaging information over a range that is larger than a corresponding acquisition range defined by the uptake value of the object to be imaged for the additional detector unit.

19. The tangible and non-transitory computer readable medium of claim 16, wherein the one or more software modules are further configured to direct the one or more processors to update the at least one boundary of the acquisition range during the primary image acquisition.

20. The tangible and non-transitory computer readable medium of claim 16, wherein the one or more software modules are further configured to direct the one or more processors to determine the at least one boundary of the acquisition range based on a change of photon counts acquired by the at least one detector unit.

* * * * *